US007598340B2

(12) United States Patent
Metchetner et al.

(10) Patent No.: US 7,598,340 B2
(45) Date of Patent: Oct. 6, 2009

(54) MONOCLONAL ANTIBODY TO A HUMAN MDR1 MULTIDRUG RESISTANCE GENE PRODUCT, AND USES

(75) Inventors: Eugene Metchetner, Palo Alto, CA (US); Igor B. Roninson, Wilmette, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 540 days.

(21) Appl. No.: 10/292,541

(22) Filed: Nov. 12, 2002

(65) Prior Publication Data

US 2003/0086931 A1 May 8, 2003

Related U.S. Application Data

(60) Continuation of application No. 09/515,232, filed on Feb. 29, 2000, now Pat. No. 6,479,639, which is a division of application No. 08/482,670, filed on Jun. 7, 1995, now Pat. No. 6,030,796, which is a division of application No. 08/032,056, filed on Mar. 16, 1993, now Pat. No. 5,773,280, which is a continuation-in-part of application No. 07/854,881, filed on Mar. 20, 1992, now Pat. No. 5,434,075.

(51) Int. Cl.
*C07K 5/00* (2006.01)
(52) U.S. Cl. ..................................... 530/300
(58) Field of Classification Search .................. 530/300
See application file for complete search history.

(56) References Cited

U.S. PATENT DOCUMENTS 5,206,352 A * 4/1993 Roninson et al. ......... 536/24.31

OTHER PUBLICATIONS

Ruth et al, Biochemistry, 2001, vol. 40, pp. 4332-4339.*
Zhou et al., Archives of Biochemistry and Biophysics, 1999, vol. 367, pp. 74-80.*
Hrycyna et al., Biochemistry, 1998, vol. 37, pp. 13660-13673.*
Kartner et al ., Science, 1983, vol. 221, pp. 1285-1288.*
Paul, William E., ed. Fundamental Immunology, Raven Press Ltd., 1993, pp. 243-247.*
Akiyama et al., "Most Drugs that Reverse Multidrug Resistance also Inhibit Photoaffinity Labeling of P-Glycoprotein by a Vinblastine Analog" *Mol. Pharm.* 33:144-147 (1987).
Bhattacharya-Chatterjee et al., "Idiotype Vaccines Against Human T cell Leukemia" *Journal of Immunology* 141:1398-1403 (Aug. 15, 1988).
Bird et al., "Single-Chain Antigen-Binding Proteins" *Science* 242: 423-426 (Oct. 21, 1988).
Borrebaeck et al., "Critical appraisal of the in vitro immunization technology for the production of mouse and human monoclonal antibodies" *Advanced Drug Delivery Reviews* 2:143-165 (1988).
Borrebaeck et al., "Human mAbs produced by primary in-vitro immunization" *Immunology Today* 9(11) 355-359 (1988).

Borrebaeck et al., "Strategy for the production of human monoclonal antibodies using in vitro activated B cells" *Journal of Immunological Methods* 123:157-165 (1989).
Bruggemann et al., "Comparison of the Effector Functions of Human Immunoglobulins Using a Matched Set of Chimeric Antibodies" *J. Exp. Med.* 166:1351-1361 (Nov. 1987).
Cenciarelli et al., "Characterization by Somatic Cell Genetics of a Monoclonal Antibody to the *MDR*1 Gene Product (P-Glycoprotein): Determination of P-Glycoptrotein Expression in Multi-Drug-Resistant KB and Cem Cell Variants" *Int. J. Cancer* 47:533-543 (1991).
Charbit et al., "Versatility of a vector for expressing foreign polypeptides at the surface of Gram-negative bacteria" *Gene* 70:181-189 (1988).
Chaudhary et al., "Expression and Activity of P-Glycoprotein, a Multidrug Efflux Pump, in Human Hematopoietic Stem Cells" 66:85-94 (Jul. 12, 1991).
Chiang et al., "Direct cDNA Cloning of the rearranged Immunoglobulin Variable Region" *BioTechniques* 7(4)360-366 (1989).
Choi et al., "An Altered Pattern of Cross-Resistance in Multidrug-Resistant Human Cells Results from Spontaneous Mutations in the mdr1 (P-Glycoprotein) Gene" *Cell* 53:519-529 (May 20, 1988).
Choi et al., "Multidrug resistance after retroviral transfer of the human MDR1 gene correlates with P-glycoprotein density in the plasma membrane and is not affected by cytotoxic selection" *Proc. Natl. Acad. Sci.* 88:7386-7390 (Aug. 1991).
Cornwell et al., "Increased Vinblastine Binding to Membrane Vesicles from Multidrug-resistant KB Cells" *Jour of Bio. Chem.* 251(17) 7921-7928 (1986).
Foon et al., "Biological Response Modifiers: The New Immunotherapy" *Cancer Research* 49:1621 (1989).
Ford et al., "Pharmacology of Drugs that Alter Multidrug Resistance in Cancer" *Pharmacological Reviews* 42(3) 155-199 (1990).
Gathuru et al., "In vitro immunization of rat spleen lymphocytes with Forssman glycosphingolipid antigen and the generation of a monoclonal antibody" *J. Immunol. Meth.* 137:95-102 (1991).
Glockshuber et al. "A Comparison of Strategies to Stabilize Immunoglobulin $F_v$-Fragments" *Biochemistry* 29:1362-67 (1990).
Hamada et al, "Functional role for the 170- to 180-kDa glycoprotein specific to drug-resistant tumor cells as revealed by monoclonal antibodies" *Proc. Natl. Acad. Sci.* 83:7785-7789 (Oct. 1986).
Hamada et al., "Mouse-Human Chimeric Antibody against the Multidrug Transporter P-Glycoprotein" *Cancer Research* 50:3167-3171 (Jun. 1, 1990).
Hoefler et al., "In situ hybridization methods for the detection of somatostatin mRNA in tissue sections using antisense RNA probes" *Histochemical Journal* 18:597-604 (1986).

(Continued)

*Primary Examiner*—Misook Yu
(74) *Attorney, Agent, or Firm*—McDonnell Boehnen Hulbert & Berghoff LLP

(57) ABSTRACT

A hybridoma (termed "UIC2 hybridoma", ATCC Accession No. HB11027) producing monoclonal antibodies (termed "UIC2 mAb") directed against an extracellular domain of a cell surface P-glycoprotein antigen associated with multidrug resistance in primate cells was produced by fusing a human myeloma cell with a spleen cell derived from a BALB/c mouse immunized with syngeneic 3T3 fibroblasts previously transfected with the isolated human mdr1 cDNA. UIC2 mAb, thus produced, as well as fragments and recombinant derivatives thereof, may be used to detect and isolate multidrug resistant primate cells and human mdr1 gene products, and to reverse multidrug resistance in primate cells, including cells of multidrug resistant human tumors.

1 Claim, 9 Drawing Sheets

OTHER PUBLICATIONS

Horio et al., "ATP-dependent transport of vinblastine in vesicles from human multidrug-resistant cells" *Proc. Natl. Acad. Sci.* 85:3580-3584 (May 1988).

Hsu et al., "Differential Overexpressing of Three mdr Gene Family Members in Multidrug-resistant J774.2 Mouse Cells" The *Journal of Biological Chemistry* 264(20)12053-62 (1989).

Huston et al., "Protein engineering of antibody binding sites: Recovery of specific activity in an anti-digoxin single-chain Fv analogue produced in *Escherichia coli*" *Proc. Natl. Acad. Sci.* 85:5879-5883 (Aug. 1988).

Jones et al., "Replacing the complementarity-determining regions in a human antibody with those from a mouse" *Nature* 321:522-525 (May 1986).

Kearney et al., "A New Mouse Myeloma Cell line that has lost immunoglobulin expression but permits the construction of antibody-secreting hybrid cell lines" *Jour. of Immunology* 123(4)1548-1550 (1979).

Kohler et al., Idiotypic Networks and Nature of Molecular Mimicry: An Overview *Methods in Enzymology* 178:3-35 (1989).

McCafferty et al., "Phage antibodies: filamentous phage displaying antibody variable domains" *Nature* 348:552-554 (Dec. 6, 1990).

Meyers et al., "Characterization of Monoclonal Antibodies Recognizing a $M_r$ 180,000 p-Glycoprotein: Differential Expression of the $M_r$ 180,000 and $M_r$ 170,000 P-Glycoproteins in Multidrug-resistant Human Tumor Cells" *Cancer Research* 49:3209-3214 (Jun. 15, 1989).

Neyfaxh et al., "Use of Flurescent Dyes as Molecular Probes for the Study of Multidrug Resistance" *Experimental Cell Research* 174:168-176 (1988).

Nilsson et al., "Intrasplenic immunization with minute amounts of antigen" *Immunology Today* 11(1)10-12 (1990).

Nolan et al., "Bifunctional antibodies: concept, production and applications" *Biochimica et Biopysica Acta* 140:1-11 (1990).

O'Brien et al. "Collateral Sensitivity of Human Multidrug-Resistant cells to Verapamil is Potentiated by Monoclonal Antibody HYB-241 Recognizing P-glycoprotein" *Proc. Amer. Assoc. Cancer Res.* 30:abs 2114 (1989).

Orlandi et al., "Cloning immunoglobulin variable domains for expression by the polymerase chain reaction" *Proc. Natl. Acad. Sci.* 86:3833-3837 (May 1989).

Pauwels et al., "Rapid and automated tetrazolium-based colorimetric assay for the detection of anti-HIV compounds" *Jour. of Viro. Methods* 20:309-321 (1988).

Pollock et al., "The Production of Human Monoclonal Antibodies By in vitro Immunization" *Laboratory Methods in Immunology* 51-60.

Queen et al., "A Humananized antobody that binds to the interleukin 2 receptor" *Proc. Natl. Acad. Sci.* 86:10029-33 (Dec. 1989).

Riechmann et al., "Reshaping human antibodies for therapy" *Nature* 332:323-327 (Mar. 24, 1988).

Schinkel et al., "Characterization of the Human MDR3 P-Glycoprotein and Its Recognition by P-Glycoprotein-specific Monoclonal Antibodies" *Cancer Research* 51:2628-2635 (May 15, 1991).

Songsivilai et al., "Bispecific antibody: a tool for diagnosis and treatment of disease" *Clin. Exp. Immunol* 79:315-321 (1990).

Tamai et al., "Competitive Interaction of Cyclosporins with the Vinca Alkaloid-binding Site of P-glycoprotein in Multidrug-resistance Cells" *Jour. of Bio. Chem.* 265(27)16509-16513 (1990).

Tsuruo et al., "Inhibition of Multidrug-resistant Human Tumor Growth in Athymic Mice by Anti-p-glycoprotein Monoclonal Antibodies" *Jpn. J. Cancer Res.* 80:627-631 (Jul. 1989).

Vaux et al., "On the Use of In Vitro Immunization for the Production of Monoclonal Antibodies" *Technique—A Journal of Methods in Cell and Molecular Biology* 2(2)72-28 (1990).

Verhoeyen et al., "Reshaping Human Antibodies: Grafting an Antilysozyme Activity" *Science* 2391534-1536 (1988).

Winter et al., "Man-made antibodies" *Nature* 349:293-299 (Jan. 24, 1991).

Young et al., "Dissection of Mycobacterium tuberculosis antigens using recombinant DNA" *Proc. Natl. Acad. Sci.* 82:2583-2587 (May 1985).

\* cited by examiner

K562/INF

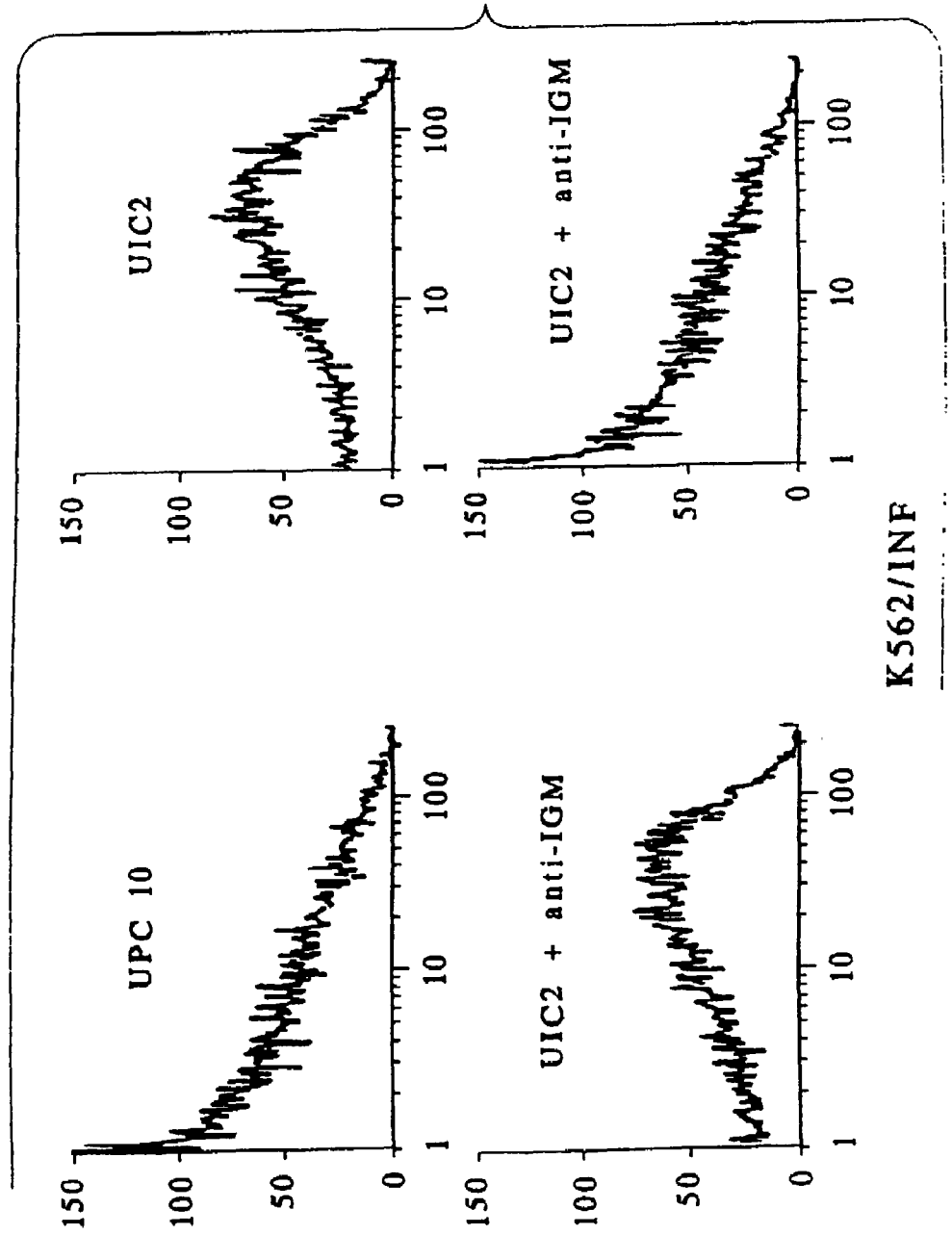

MONOCLONAL ANTIBODY TO A HUMAN MDR1 MULTIDRUG RESISTANCE GENE PRODUCT, AND USES

This application is a continuation of U.S. Ser. No. 09/515,232, filed Feb. 29, 2000, now U.S. Pat. No. 6,479,639, issued Nov. 12, 2002, which is a divisional application of U.S. Ser. No. 08/482,670, filed Jun. 7, 1995, now U.S. Pat. No. 6,030,796, issued Feb. 29, 2000, which is a divisional application of U.S. Ser. No. 08/032,056, filed Mar. 16, 1993, now U.S. Pat. No. 5,773,280, issued Jun. 30, 1998, which is a continuation-in-part of U.S. Ser. No. 07/854,881, filed Mar. 20, 1992, now U.S. Pat. No. 5,434,075, issued Jul. 18, 1995.

This invention was made with government support under research grant CA40333 awarded by the National Institutes of Health. The government has certain rights in this invention.

BACKGROUND

1. Field of the Invention

The present invention relates to a hybridoma that produces monoclonal antibodies specific to a cell surface antigen associated with multidrug resistance in human cells, and uses of such antibodies and their fragments or recombinant derivatives.

2. Description of the Related Art

Many human cancers express intrinsically or develop spontaneously resistance to several classes of anticancer drugs, each with a different structure and different mechanism of action. This phenomenon, which can be mimicked in cultured mammalian cells selected for resistance to certain plant alkaloids or antitumor antibiotics such as colchicine, vinblastine and doxorubicin (former generic name is adriamycin), is generally referred to as multidrug resistance ("MDR").[1] This MDR phenotype presents a major obstacle to successful cancer chemotherapy in human patients.

MDR, in most cases, appears to result from decreased intracellular accumulation of drug as the result of increased drug efflux related to alterations in a plasma membrane mechanism. When mutant cell lines expressing MDR are isolated, they are seen to express an ATP-dependent pump mechanism located in the plasma membrane that keeps the intracellular accumulation of an anti-cancer drug low. This mechanism consists of active extrusion of the drug, which had originally entered through the plasma membrane.

The gene encoding this pump system, sometimes referred to as the multidrug transporter, has been cloned from cultured human cells by Roninson et al. (see reference 12 below), and is generally referred to as mdr1 or MDR1.[1] This gene is expressed in several classes of normal tissues[1], but physiological substrates transported for the mdr1 gene product in these tissues have not been identified.

The protein product of the mdr1 gene, generally known as P-glycoprotein ("P-170", "Pgp"), is a 170 kDa trans-plasma membrane protein that constitutes the aforementioned energy-dependent efflux pump. Expression of Pgp on the cell surface is sufficient to render cells resistant to multiple cytotoxic drugs, including many anti-cancer agents. Pgp-mediated MDR appears to be an important clinical component of tumor resistance in tumors of different types, and mdr1 gene expression correlates with resistance to chemotherapy in different types of cancer.

Sequence analysis of the mdr1 gene indicates that Pgp consists of 1280 amino acids distributed between two homologous (43% identity) halves.[1] Each half of the molecule has six hydrophobic transmembrane domains and each has an ATP binding site within the large cytoplasmic loops. Only about 8% of the molecule is extracellular, and the carbohydrate moiety (approximately 30 kDa) is bound to sites in this region.

With the advent of knowledge about the central role in MDR played by Pgp, agents with a potential for reversing MDR have been targeted at Pgp. Several classes of drugs, including calcium channel blockers, e.g., verapamil, immunosuppressants such as cyclosporines and steroid hormones, colmodulin inhibitors and several other compounds, were found to enhance the intracellular accumulation and cytotoxic action of Pgp-transported drugs.[2] Many of these agents were found to inhibit drug binding or transport by Pgp.[3] Some of these agents themselves were found to bind to and be effluxed by Pgp[4], suggesting that their enhancing effects on the cytotoxicity of Pgp substrates are due, at least in part, to competition for drug binding sites on this protein, rather than to effects on its function.

Certain of these agents may have additional intracellular pleiotropic effects in MDR cells that may limit their applicability as specific inhibitors of the efflux pump action of Pgp. Furthermore, most of the known MDR-reversing drugs used in clinical trials have major side effects unrelated to inhibition of Pgp, such as calcium channel blockage (verapamil) or immunosuppression (cyclosporines and steroids), which restricts their clinically achievable dosage.

The use of anti-Pgp antibodies to circumvent Pgp-MDR offers the prospect of specificity, as the antibodies should target only Pgp, and the only toxicity should be that potentially arising from the administration of a protein. Furthermore, antibody binding is likely to have a more-prolonged inhibitory effect than would transient binding of a competitive inhibitor.

Only antibodies that react with an extracellular epitope of Pgp would be able to react with the efflux pump protein in the plasma membrane of intact cells and potentially influence, i.e. reverse, MDR. Antibodies directed to the cytoplasmic portion of Pgp, such as C219[5], are unlikely to be useful for reversal of MDR.

Monoclonal antibodies ("mAb"), termed MRK-16 and MRK-17, were produced by immunizing mice with doxorubicin-resistant K-562 human leukemia cells; both antibodies recognized Pgp.[6] MRK-16 mAb modulated vincristine and actinomycin D transport in resistant cells, and MRK-17 mAb specifically inhibited the growth; of the resistant cells. MRK-16 mAb increased the in vivo toxicity of vincristine to a human MDR cell line (colon cancer) grown as a xenograft in nude mice.[7] The in vitro potentiation of drug cytotoxicity by MRK-16 mAb was, however, weak relative to known chemical inhibitors of Pgp action, and was apparently limited to only two Pgp substrates (vincristine and actinomycin D), having no effect on cytotoxicity by doxorubicin.[6] Treatment with MRK-16 mAb of athymic mice previously inoculated with drug resistant human ovarian cancer cells $2780^{AD}$ caused regression of established subcutaneous tumors.[8] A recombinant chimeric antibody that combines the variable region of MRK-16 with the Fc portion of human antibodies was reported to be more effective than parent MRK-16 mAb in increasing cytotoxicity in vitro.[9]

Monoclonal antibodies HYB-241 and HYB-612, which recognize an external epitope of Pgp, have been reported to increase the accumulation of vincristine and actinomycin D in tumor cells and to increase the cytotoxicity of combinations of these drugs with verapamil.[10]

A mouse $IgG_{2a}$ mAb, termed MAb657, has been reported to react with mdr1 gene-expressing cells and with MDR human cells.[11] Although this mAb was shown to increase the susceptibility of MDR cells to cytotoxicity mediated by human peripheral blood lymphocytes, it is not known to have an inhibitory effect on the drug efflux pump function of Pgp.

As will be detailed in the description of the invention below, the effects of the mAb of the present invention can be distinguished from those of MRK-16, HYB-241 and HYB-612 mAbs on many levels, including effects on inhibition of rhodamine 123 efflux from MDR cells, potentiation of the effects of vinblastine on cell growth and colony formation, potentiation of the cytotoxic effect of doxorubicin, epitopic specificity and detergent sensitivity.

An important need remains for novel monoclonal antibodies that recognize extracellular domains of human Pgp on the surface of intact cells, that exhibit strong inhibitory effects on Pgp-mediated efflux of anti-cancer drugs from human tumor cells, that reverse resistance to a wide variety of cytotoxic drugs that are transported by the human Pgp system, and that are at least as potent as commonly used chemical inhibitors of Pgp but without undesirable side effects. A hybridoma producing such a specific mAb has been produced, and the properties and uses of this antibody, as well as fragments and recombinant derivatives thereof, are described below.

SUMMARY OF THE INVENTION

The invention comprises the novel hybrid continuous cell line termed "UIC2" (ATCC Accession No. HB11027, deposited with the American Type Culture Collection, 12301 Parklawn Drive, Rockville, Md. 20852 on Apr. 28, 1992) and the novel mAb produced by this hybridoma (termed "UIC2 mAb") that is directed to an extracellular epitope of the human MDR trans-plasma membrane Pgp in such a manner so as to strongly inhibit Pgp drug efflux function and thereby increase the cytotoxicity potential of anti-cancer drugs in human MDR cells.

In one aspect of the invention, the UIC2 hybridoma is produced.

In another aspect of the invention, UIC2 mAb is produced, such mAb having the aforementioned characteristics, wherein the target antigen is human cell surface Pgp encoded by the human mdr1 gene.

In yet another aspect of the invention, fragments of UIC2 mAb are disclosed, including complementarity-determining heavy and light chains and variable and constant regions thereof.

In still another aspect of the invention, recombinant derivatives of the UIC2 mAb are disclosed, including recombinant antibodies with the specificity of UIC2 mAb, such as humanized mAb, bifunctional mAb, isolated $V_H$ and $V_L$ antibody regions, linear mAb chains containing $V_H$ and $V_L$ regions, fragments of these molecules, and cDNA encoding such recombinant derivatives.

In still another aspect of the invention, UIC2 mAb is used to produce anti-idiotype antibodies directed against the site on UIC2 mAb that is complementary to the epitopic site of Pgp to which UIC2 mAb binds, as well as to produce anti-anti-idiotype antibodies.

In another aspect of the invention, methods are provided for identifying the extracellular epitopic site(s) of Pgp to which UIC2 mAb binds, and amino acid sequences from such sites are used to raise antibodies with the binding characteristics and functional specificities of UIC2 mAb.

In yet another aspect of the invention, methods are provided for using the UIC2 mAb, or a fragment or recombinant derivative thereof to diagnose or isolate multidrug resistant primate tumor cells, as well as to isolate gene products of the human mdr1 gene from mixtures of biomolecules.

In another aspect of the invention, reagents are provided that incorporate the UIC2 mAb, fragments or recombinant derivatives thereof of the invention in pharmaceutical compositions that are useful for immunotherapy of subjects bearing multidrug resistant tumors and for reversing the drug-efflux effects of Pgp.

These and other aspects will become evident by reference to the description of the invention and the appended claims.

DESCRIPTION OF THE DRAWINGS

FIGS. 2A, 2B and 2C shows the effect of mAb UIC2 on efflux of a fluorescent P-glycoprotein substrate Rhodamine 123 from CEM/VLB$_{100}$ (A) and K562/Inf (B) multidrug-resistant cells, and the effect of preadsorption of UIC2 mAb with anti-IgG or anti-IgM antisera on Rhodamine 123 efflux (C).

DETAILED DESCRIPTION OF THE INVENTION

Figure 1:
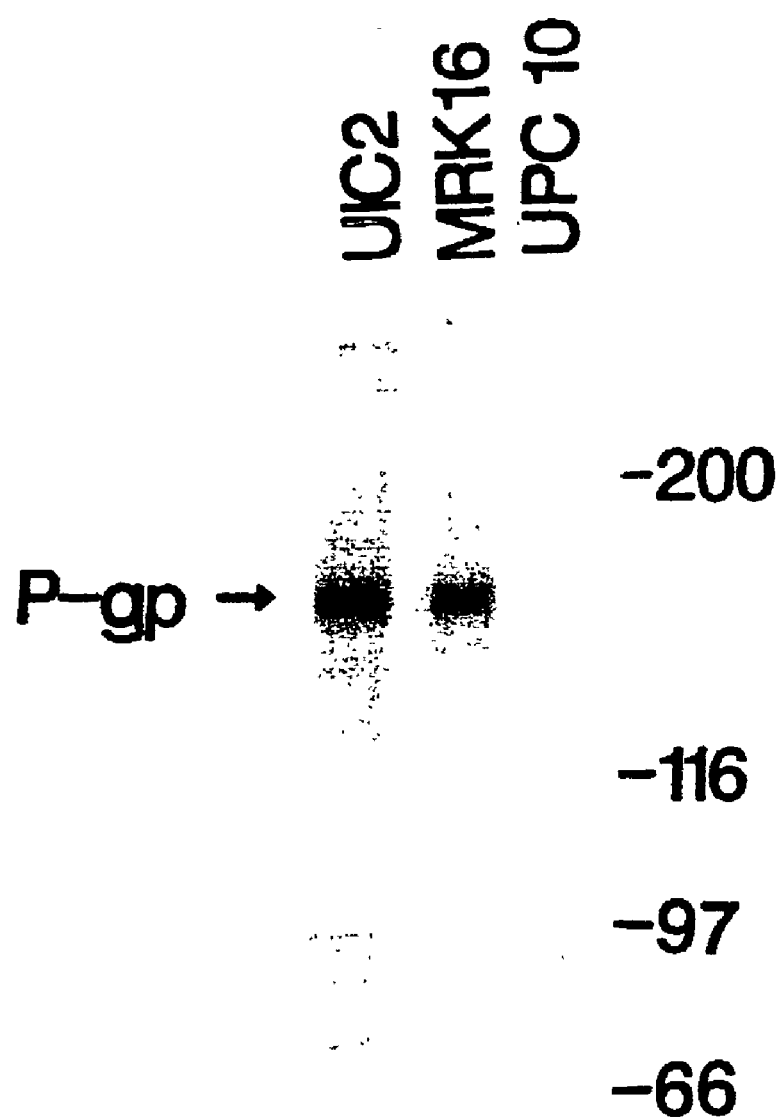
FIG. 1 shows the results of immunoprecipitation of P-glycoprotein with UIC2 mAb. Immunoprecipitation of P-glycoprotein from multidrug-resistant BALB/c 3T3-1000 cells with UIC2 mAb, MRK-16 mAb or UPC10 (IgG2a control) was carried out as described in Example 7. The 170-180 kDa band specific to UIC2 mAb and MRK-16 mAb is indicated by an arrow.

Co-owned U.S. Pat. No. 5,206,352 to Roninson et al., which is incorporated herein by reference, discloses the sequence of the isolated human mdr1 gene that specifically hybridizes with human mature mRNA transcribed from a human mdr1 gene.[12] As discussed above, the polypeptide encoded by this human mdr1 gene is P-glycoprotein, also referred to as Pgp or P-170. Only a small portion (about 8%) of this protein, including all of the 30 kDa of carbohydrate, is believed to be extracellular.[1]

In co-owned U.S. Pat. No. 5,206,352, polyclonal and monoclonal antibodies against Pgp encoded by the human mdr1 gene are produced by immunization of animals with chemically-synthesized Pgp fragments predicted from the gene sequence, or with Pgp produced by prokaryotic or eukaryotic expression systems. In the present invention, a specific transfected, overexpressing line of multidrug resistant human cells is used as the immunogen in order to produce a hybridoma that produces a mAb directed to a specific extracellular Pgp epitope on human multidrug resistant cells.

For the purposes of the present invention, multidrug resistance is defined as cross-resistance to the following cytotoxic drugs: vinblastine, vincristine, doxorubicin, colchicine, actinomycin D, etoposide, taxol, puromycin, and gramicidin D.

The mAb of the present invention, which, as noted above, is directed to an epitope in an extracellular domain of the human mdr1 gene product Pgp, is made by a process that uses, as the primary immunogen for immunizing mice, cells that have been made MDR by transfection with the isolated human mdr1 cDNA of the aforementioned copending U.S. Ser. No. 622,836.[12] Immunogen cells for immunization of BALB/c mice are preferably transfected syngeneic mouse fibroblasts, that is, transfected BALB/c mouse 3T3 fibroblasts. MDR derivatives of mouse BALB/c 3T3 fibroblasts are generated with human mdr1 cDNA using a mammalian expression vector, preferably the pUCFVXMDR1 plasmid developed by one of the present inventors.[13] As the MDR phenotype is unstable in the most highly resistant cells, cells grown in the absence of a drug will exhibit a decrease in resistance. Hence, it is preferred to maintain transfected cells in growth media also containing a maintenance concentration of the drug that is to be used for selection, e.g., 20 µg/ml vinblastine.

Following transfection, 3T3 BALB/c fibroblast derivatives, in which the transfected mdr1 gene has been amplified, are produced by consecutive steps of selection in progressively higher concentrations of a drug to which the transfected cells are resistant. This procedure enables the selection of highly multidrug resistant 3T3 BALB/c fibroblasts that express large amounts of Pgp and insertion of this molecule into the plasma membrane of the cells. Cells may be selected for desirable resistance to vinblastine by consecutive incubation of fibroblast cultures in 250 ng/ml, 500 ng/ml and 1000 ng/ml of the drug. For convenience, such cells are labeled BALB/c 3T3-250, BALB/c 3T3-500 and BALB/c 3T3-1000, respectively. BALB/c 3T3-1000 selectant cells that express the highest level of mdr1 gene product are highly preferred for immunization of host BALB/c mice.

Mouse cells (e.g., BALB/c 3T3 cells) transfected with human mdr1 cDNA are used to immunize syngeneic (e.g., BALB/C) mice. Appropriate numbers of cells are injected subcutaneously (s.c.) or intraperitoneally (i.p.) by art-recognized immunization protocols. Typically, $10^5$ to $10^8$ transfected cells are injected 5 or 6 times at two week intervals, and a final boosting is done with, for example, $10^6$ cells subcutaneously and/or intravenously. At an appropriate time after the booster injection, typically 3 to 5 days thereafter, the spleen is harvested from a hyperimmune mouse, and hybridomas generated by standard procedures[14], using human myeloma cells, P3-X63-Ag 8.653 (ATCC, Manassas, Va.).

Extracellular fluids from individual hybridoma cultures are screened for specific mAb production by conventional methods, such as by indirect immunofluorescence using control cells that do not express human Pgp (i.e., non-transfected BALB/c 3T3 fibroblasts) and human Pgp-expressing (i.e., BALB/c 3T3-1000) cells affixed to glass slides, and FITC-labeled goat anti-mouse polyvalent immunoglobulins (Sigma Chem. Co., St. Louis, Mo.) as the secondary, reporter antibody. The particular screening method is not critical provided that it is capable of detecting anti-human mdr1 Pgp mab. It is important, however, that cells are not permeabilized during screening, so that only antibodies reactive with extracellular protein domains will be detected.

A stable hybridoma may be established by conventional methods, such as by consecutive rounds of subcloning by, e.g., end-point dilution, and screening the culture medium for monoclonal antibodies. The hybridoma is propagated by, for example, growth in ascites fluid in vivo in syngeneic animals, and the secreted antibody isolated and purified from ascites fluid by affinity chromatography with a Sepharose-Protein A matrix specific for IgG isotype. Other procedures for immunoglobulin purification that are well known in the art are also usable, such as by adsorption to affinity-purified goat anti-mouse IgG under conditions (e.g., ice-bath temperatures) of maximum adsorption of mAb to the second antibodies.

The mAb produced by the aforementioned hybridoma, as well as fragments and recombinant derivatives thereof to be described below, may be characterized as to immunoglobulin isotype by art-recognized double immunodiffusion Ouchterlony and immunoblotting tests using mouse IgG subclass-specific antisera.

MAb, fragments and recombinant derivatives thereof may be characterized for reactivity with different Pgp-expressing cell lines by any convenient technique, for example, by indirect immunofluorescence immunolabeling followed by any technique suitable for detecting antibody-cell interactions, such as by flow cytometric analysis or microscopy. Other immunocytochemical techniques may also be used.

MAb, fragments and recombinant derivatives thereof may be tested for binding to Pgp in MDR cells by immunoprecipitation methods. For example, MDR cells (e.g., $5\text{-}10 \times 10^6$ cells) may be incubated (e.g., 10-18 hours at 37° C.) with a radioactive essential amino acid, such as $^{35}$S-methionine and the like, so as to radioactively label the Pgp protein. Labeled cells are then incubated with a purified antibody preparation until binding sites on cells are saturated. Cells are then lysed with a detergent that solubilizes Pgp out of plasma membranes, but that does not dissociate mAb from Pgp. To inhibit proteolysis by endogenous cellular proteases, a protease inhibitor such as 0.1 mM phenylmethylsulfonyl fluoride ("PMSF") may be added to the detergent. While a variety of detergents may be employed to solubilize Pgp out of the cell's plasma membrane, deoxycholic acid (0.2 to 1%) is highly preferred for UIC2 mAb as it does not dissociate the mAb-Pgp complex. MAb-Pgp complexes may be isolated from the lysate by any convenient adsorption method, such as immunoadsorption of this (IgG-type) mAb with immobilized Protein A; this latter protein is a specific adsorbent for IgG immunoproteins. MAb-Pgp complexes may then be separated by SDS-PAGE, and mAb-containing sites detected by, e.g., Western blotting using labeled goat anti-mouse IgG antibody conjugated to a reporter molecule, such as alkaline phosphatase and the like (Fisher Scientific, Pittsburg, Pa.). Preparative isolation of human mdr1 gene products may be carried out by similar techniques in which the adsorbent for gene products is an immobilized antibody of the invention.

The effect of an anti-Pgp mAb, fragment or recombinant derivative thereof on Pgp function may be assessed by studying the efflux of fluorescent or radioactively labeled drugs from MDR cells in the presence or absence of mAb. In a preferred assay[15], suspensions of mammalian cells (e.g., $10^5$ to $10^7$ cells) expressing Pgp are incubated at ice-bath temperatures with the test antibody preparation in serum-free buffer medium. Treated cells are then loaded with a marker dye, e.g., Rhodamine-123 ("Rh123") (0.1-10.0 µg/ml) or doxorubicin (1-10 µM) by incubation with the dye at ice-bath temperatures. Dye-loaded cells are then incubated at 37°, preferably with the aforementioned antibody preparation in the medium in order to maintain saturation of cell surface Pgp with antibody, and efflux of dye measured by assessing dye retention by cells by a flow cytometric-fluorescence method.

The effects of antibody preparations of the invention on drug cytotoxicity may be assessed by incubating suspensions of MDR and control cells with the antibody preparation, then testing for cell growth inhibition by colony formation, plating efficiency, and/or MTT growth inhibition assay[13,16] in the absence and presence of an anti-cancer drug such as one of the vinca alkaloids. BALB/c 3T3-1000 fibroblasts are particularly suitable for plating efficiency assays and the MDR cell line K562/inf for the growth inhibition assay. The effects of antibody preparations on drug cytotoxicity may be assayed by incubating cell suspensions with a purified antibody preparation, and plating cells in microtitre plate wells for colony or growth inhibition assays in the presence of the antibody preparation.

The ability of the antibody preparations of the invention to induce complement-mediated cytotoxicity may be tested by art-recognized assays using, e.g., complement from rabbit sera.[17]

In accordance with this invention, mAb against human mdr1 Pgp immunogens may be produced by methods alternate to the mouse in vivo immunization-spleen cell-human myeloma methods discussed above in connection with the production of the UIC2 hybridoma. In one embodiment, intrasplenic immunization with cells expressing the human mdr1 gene may be used to produce immunized splenocytes for production of hybridomas. See, e.g., reference 18, which is incorporated herein by reference.

In another embodiment, in vitro immunization may be carried out wherein cells expressing the human mdr1 gene are presented to a spleen cell culture and, after a suitable period, typically a week, cell fusion with mouse or human myeloma cells is carried out to produce hybridomas. See, e.g., reference 19, which is incorporated herein by reference.

In addition to the mAb produced by the UIC2 hybridoma of the invention (see Example 3 below), genetic information derived from these cells may be used to produce recombinant derivative antibodies useful for both diagnostic and therapeutic applications. Such recombinant derivatives can be readily produced through art-recognized methods of genetic engineering, as reviewed in reference 20, which is incorporated herein by reference.

In a preferred procedure, polynucleotide sequences encoding the variable regions of the heavy and the light chains of UIC2 mAb are prepared by polymerase chain reaction (PCR) using primers derived from constant regions of the corresponding chains.[21] Genomic DNA, extracted from the UIC2 hybridoma cell line, is used as the template for PCR. Alternatively, cDNA, synthesized from mRNA of UIC2 hybridoma by standard procedures[22], may be used as the PCR template. The $V_H$ and $V_L$ regions of UIC2 mAb, amplified by PCR, are sequenced either directly or after cloning into a suitable vector. The derived sequence information is highly valuable, as the $V_H$ and $V_L$ regions carry all the determinants of the antibody specificity, which can then be transferred to other antibodies or other recombinant molecules by standard genetic engineering techniques. cDNA encoding the heavy and the light chains of UIC2 mAb may also be isolated by preparing a cDNA library and screening such a library with commonly available probes corresponding to constant regions of immunoglobulin heavy and light chains.

To obtain recombinant antibodies with the specificity of UIC2 mAb, the aforementioned isolated $V_H$ and $V_L$ cDNA sequences are inserted into an expression vector, where they are joined in frame with the cDNA sequences for the corresponding constant regions of either human or mouse immunoglobulin chains. For example, M13 phage vectors M13-VHPCR1 and M13-VKPCR1[21] may be used to generate chimeric human-mouse heavy and light antibody chains. Such chimeric antibodies are preferred over entirely mouse-derived antibodies for in vivo administration to a patient for diagnostic or therapeutic purposes. The choice of the constant regions to be spliced with the variable regions of UIC2 mAb is directed by the intended use of the recombinant antibody. Thus, the human gamma 1 isotype would give rise to antibody efficient in complement-mediated and cell-mediated killing of target cells.[17,23] In contrast, the constant region of the gamma 4 isotype is preferred if the antibody is intended for diagnostic use (such as in vivo imaging) or for enhancing the cytotoxic effect of P-glycoprotein transported drugs, without inducing other types of cytotoxicity. It is also possible to generate "humanized" antibodies with the specificity of UIC2 by antibody "reshaping"[20], i.e., grafting the antigen-binding loops of the V domains of UIC2 mAb onto V regions of a cloned human antibody.[17,23-26]

Recombinant derivatives of UIC2 mAb may be used within an appropriate expression vector to produce bulk quantities of corresponding proteins in prokaryotic (e.g., bacterial) or eukaryotic (yeast, mammalian or insect) cells expression systems well known in the art.[22]

Fragments of the UIC2 mAb, maintaining the antigen specificity of the complete antibody, may be derived by enzymatic, chemical or genetic engineering techniques. For example, purified UIC2 mAb may be fragmented by partial digestion with proteolytic enzymes, such as papain or trysin.[27] Papain digestion produces two Fab fragments and one Fc fragment. Purified UIC2 mAb can also be cleaved with pepsin which releases $F(ab)_2$ (two antigen-binding domains bound together). The resulting Fab or $F(ab)_2$ fragments of UIC2 mAb may be purified away from any remaining intact antibody and Fc fragments by chromatography on Protein A or by any other immunochemical method (ibid.).

Fragments of the UIC2 mAb may also be derived by genetic engineering techniques, using the isolated cDNA sequences that encode the variable (V) regions of UIC2 mAb. Thus, a fragment corresponding to the variable heavy chain ($V_H$) region alone may be used as a single-domain antibody[28], for specific high-affinity binding to P-glycoprotein. Sub-fragments of the $V_H$ domain may also be used for specific binding to the antigen.[20] The $V_H$ and variable light chain ($V_L$) domains may also be used to generate Fv fragments, either chemically through bisulfide linkage[29] or by genetically linking $V_H$ and $V_L$ domains possibly via a hydrophobic flexible peptide to generate a single-chain Fv fragment.[30]

Fragments of UIC2 mAb, lacking the constant (Fc) portion, may be advantageous over the complete antibody for in vivo applications, as such fragments are likely to possess improved tissue permeability. Furthermore, many cells and tissues in the body express receptors capable of binding to the Fc portion of antibodies, resulting in undesirable non-specific binding of the complete antibody.

UIC2 mAb, a complementarity-determining fragment or recombinant derivative thereof can be coupled with a chemotherapeutic drug, an animal or plant toxin, a radioactive isotope, etc. using either chemical or genetic engineering techniques, as reviewed in references 20 and 31, which are incorporated herein by reference.

The specificity-determining domains of UIC2 (such as a single-chain Fv fragment) may also be used to generate recombinant virus particles that would specifically bind to Pgp. Thus, a single-chain Fv fragment of UIC2 mAb described above may be inserted at the N-terminal region of the gene III protein of fd bacteriophage or another filamentous phage, and "phage antibody" generated, as described by reference 32, which is incorporated herein by reference. As gene III protein of fd bacteriophage has four sites into which foreign peptides can be spliced, bi-functional phage antibodies may be developed by simultaneously inserting into this protein fragments of UIC2 mAb and of some other protein with a desired second specificity (antibody fragment or enzyme). The specificity-determining domains of UIC2 mAb may also be inserted into a protein expressed on the outer surface of some other prokaryotic or eukaryotic virus. It is also possible to insert such a domain into a protein normally expressed on the surface of a prokaryotic or eukaryotic cell, such as LamB protein of *Escherichia coli*[33], for the purpose of targeting the recipient cells to Pgp.

The UIC2 hybridoma may also be used for constructing hybrid hybridomas capable of secreting hybrid bispecific antibodies.[20,34] In one embodiment, UIC2 hybridoma cells are fused, using conventional cell fusion technology, with another hybridoma cell line producing mAb against an antigen that may be useful for diagnostic and/or therapeutic purposes in combination with UIC2 mAb (such antigens being enzymes used in immunochemical assays, cytotoxins, fluorescent dyes, etc.). UIC2 hybridoma cells may also be hybridized with spleen cells from an animal immunized with the second antigen, or with in vitro activated lymphocytes, or lymphocytic cell lines.[15] Either animal (for example, mouse, rat or hamster) or human cells may be used as fusion partners for hybrid hybridoma production. The desired bi-functional antibodies can be separated from UIC2 mAb and the partner antibody by conventional methods.[27]

The subject invention is not intended to be limited in scope to the UIC2 hybridoma deposited, but this hybridoma is intended as a single illustration of hybridomas that produce a Pgp extracellular epitope-specific mAb that interacts competitively with the same epitope as does the UIC2 mAb, and that is the functional equivalent of UIC2 mAb as function is defined above and in the following examples.

UIC2 mAb may also be used as an immunogen to obtain specific anti-idiotype antibodies, using methods well known in the art.[36] Such anti-idiotype antibodies will be directed against the UIC2 mAb antigen-binding site. Such binding sites can mimic in their structure the epitope of Pgp that is reactive with, i.e., complementary to, UIC2 mAb. Anti-idiotype antibodies of UIC2 mAb or their derivatives or fragments will be useful as vaccine preparations to elicit an immune response against Pgp, as an approach to stimulating a host response against MDR tumors. Further, anti-idiotype antibodies may also be used as immunogens to obtain anti-anti-idiotype antibodies. Such anti-anti-idiotype antibodies are likely to possess the same epitope specificity and functional effects as the original UIC2 mAb, and consequently can be viewed as derivatives of that antibody. In particular, human cell lines producing anti-anti-idiotype antibodies with the specificity of UIC2 mAb may be generated by in vitro immunization of peripheral β-lymphocytes with an anti-idiotype antibody against UIC2 mAb using established techniques.[36] This procedure produces entirely human (rather than humanized) mAbs with the specificity and biological efficacy of UIC2 mAb. The utility of anti-idiotype antibodies as vaccines, and the ability of anti-anti-idiotype antibodies to mimic the antigen specificity of the original antibody, are well known in the art.[37]

UIC2 mAb recognizes a specific epitope of Pgp, distinct from ones recognized by mAbs that, unlike the present mAb, are unable to inhibit or reverse MDR. The particular region(s) of Pgp comprising the UIC2 mAb epitope can be identified by testing the reactivity of this mAb with a series of short synthetic peptides contained within human Pgp, particularly the extracellular domains of Pgp. By this means, the epitope of MRK-16 mAb has been mapped to the first and fourth of the six predicted extracellular peptide loops of Pgp.[38] Alternately, protein sequences comprising the UIC2 epitope may be determined by using UIC2 mAb as a probe to screen a library of short random fragments of mdr1 cDNA in an appropriate expression vector, such as λ gt11[39] or a vector that expresses inserted peptides as parts of a fusion protein with LamB, a surface protein of E. coli.[33] In yet another embodiment, epitopic sites for UIC2 mAb may be identified by testing the binding of this mAb to a series of transfectant MDR cell lines, each having a variant mdr1 Pgp containing a known deletion in an extracellular loop. Failure of the mAb to react with a particular Pgp variant indicates that the deleted peptide fragment either constitutes or forms part of the recognition site of UIC2 mAb or that it affects a conformation essential for recognition. Once the epitope(s) is (are) identified by the aforementioned procedures, amino acid sequences from such sites can be used to raise additional antibodies, preferably monoclonal antibodies with the specificity of UIC2 mAb.

The UIC2 mAb of the invention or its complementarity-determining fragments or recombinant derivatives may be used in immunodiagnosis and immunotherapy of subjects bearing MDR tumors, particularly as described below.

Immunodiagnosis

UIC2 mAb, complementarity-determining fragments or recombinant derivatives thereof may be used as specific and sensitive reagents for the detection of MDR cells both ex vivo or in vivo.

In direct immunoassay methods for the identification and/or quantification of MDR cells, suspended or immobilized (culture plate) cells, or tissue sections or other cytological or histological preparations, are incubated with the UIC2 mAb, a fragment or recombinant derivative thereof, covalently labeled with a reporter molecule. A wide variety of reporter molecules are known in the immunology arts, and include fluorophores, chromagens, chemiluminescers, enzymes, avidin-biotin systems, radioactive atoms, and the like. Incubation conditions for maximum binding may be selected without undue experimentation. Typically, cells in buffer are incubated with the labeled antibody in the cold (e.g., 4° C.) for from 30 to 60 minutes. After isolating and washing the cell-labeled antibody complex, the label is detected or quantified by art-recognized techniques. Alternately, the primary antibody (i.e., UIC2 mAb, fragment or derivative) is not labeled, and detection is had by means of a labeled second reagent, such as anti-immunoglobulin antibody or $F(ab)_2$ fragment conjugated with a reporter molecule.

Alternatively, MDR cells are detected by immunofluorescence microscopy. Cell suspensions, suspected of being or containing MDR cells, are obtained from patients and are grown in plastic culture dishes. Cells are then contacted with the UIC2 mAb, fragment or recombinant derivative of the invention under conditions of maximum binding. Such conditions are readily and routinely determinable without undue experimentation. After washing the immobilized cell-antibody conjugate with a buffer to remove unbound materials, the conjugate is then contacted with a fluorophore-labeled second antibody (e.g., rhodamine-labeled goat anti-mouse IgG). Cells are then washed, fixed in formalin or another appropriate fixative, and examined in a fluorescence microscope.[15] The amount of fluorescence, and, consequently, the number of MDR cells present in the sample, may be quantified using a standard image-analysis instrument. Where a fragment or recombinant derivative of UIC2 mAb is used, an appropriate second antibody may have to be used.

The UIC2 mAb, complementarity-determining fragments and recombinant derivatives of the invention may also be used in art-recognized methods for immunocytochemical staining of tumor sections suspected of containing MDR cells, a technique that can be combined with in situ hybridization with a mdr1 polynucleotide probe on the same slide (see, e.g., reference 40, the immunocytochemical methods from which are incorporated by reference).

Immunotherapy

In one embodiment of the invention, UIC2 mAb, or a complementarity-determining fragment or recombinant derivative thereof, in a pharmaceutically acceptable vehicle (such vehicles are described in reference 41, which is incorporated herein by reference), may be administered to a subject primate by an appropriate route, such as parenterally. Therapeutic effects are based on the ability of such antibody preparations to target MDR tumor cells, bind strongly to an extracellular domain of the surface Pgp molecule of such cells, and thereby inhibit the drug efflux mechanism induced by this transmembrane protein. In this therapeutic modality, an anti-cancer drug may be administered concurrently to or sequentially with an antibody or antibody-cytotoxin complex of the invention.

In another embodiment, the antibody or fragment or recombinant derivative thereof is administered to a subject bearing an MDR tumor in a pharmaceutically acceptable vehicle to induce complement-mediated or antibody-mediated cytotoxicity to the tumor through the effector portion of the antibody molecule.

In a third embodiment, the antibody preparation is first covalently conjugated with a cytotoxic agent such as doxorubicin or a radioisotope, or both, and the conjugate, in a pharmaceutically acceptable vehicle, then administered to a subject primate bearing an MDR tumor. This embodiment produces combined therapeutic effects wherein the antibody targets MDR cells, the antibody inhibits Pgp-mediated efflux of drugs, and the cytotoxin destroys the targeted cells.

The above-described modalities for selective destruction of MDR tumor cells using UIC2 mAb or its derivatives can be used, not only for in vivo administration, but also for ex vivo chemotherapy. Ex vivo chemotherapy may be used, for example, as the means by which a patient's bone marrow may be purged of tumor cells in cancer therapeutic protocols that involve autologous bone marrow transplantation. That is to say, a sample of a patient's bone marrow is withdrawn from the body, the suspension is treated with UIC2 mAb or one of the aforementioned cytotoxic derivatives in order to destroy MDR cells, and the treated bone marrow is then returned to the patient.

The following examples provide preferred embodiments of the invention which are not to be construed as in any way limiting the scope of the invention as recited in the appended claims.

EXAMPLE 1

Multidrug Resistant Cell Lines

Mouse fibroblast BALB/c 3T3 cells expressing the mdr1 transmembrane Pgp were derived by transfecting fibroblasts with isolated human mdr1 cDNA[12] in a eukaryotic expression vector pUCFVXMDR1[13], isolating multidrug-resistant cells in 20 ng/ml of vinblastine, and subsequently amplifying the transfected gene by consecutive steps of selection in 250 ng/ml, 500 ng/ml and 1000 ng/ml of vinblastine. The resultant multidrug-resistant fibroblasts were termed BALB/c 3T3-250, BALB/c 3T3-500 and BALB/c 3T3-1000, respectively.

The K562/Inf cell line was derived by infection of human K562 leukemia cells with a recombinant retrovirus pLMDR1L6 carrying human mdr1 cDNA[42], and subsequently subcloning without cytotoxic selection.

The LRMN1 cell line was obtained by transfection of the CHO LR73 fibroblast cell line with plasmid pUCFVXMDR1/neo that expresses human mdr1 cDNA and the neo (G418 resistance) gene, followed by selection with G418 and testing individual transfectants for increased efflux of Rh123.

MDR cell lines KB-8, KB-8-5, KB-8-5-11 and KB-V1, isolated from human KB-3-1 carcinoma cells by multistep selection with colchicine or vinblastine, were obtained from Dr. Michael M. Gottesman, National Institutes of Health, Bethesda, Md.

KB-GRC1 cells were derived from KB-3-1 by transfection with pUCFVXMDR1[13], and selection using colchicine.

CEM/VLB$_{100}$ cells, derived from human CEM leukemia cells by multistep selection with vinblastine, were obtained from Dr. W. T. Beck, St. Jude's Children's Hospital, Memphis, Tenn.

Vinblastine- or colchicine-selected MDR derivatives of mouse J774.2 macrophage cell line, J7-V2-1, J7-V3-1 and J7-C1-100, were obtained from Dr. S. B. Horwitz, Albert Einstein College of Medicine, Bronx, N.Y. These cell lines in their combination overexpress all three mouse mdr genes, mdr1a, mdr1b and mdr2.[43]

EXAMPLE 2

Monoclonal Antibodies

MRK-16 mAb (IgG$_{2a}$) was obtained from Dr. T. Tsuruo, University of Tokyo, Japan. HYB-241 and HYB-612 mAb (IgG$_1$) were obtained from Dr. L. Rittmann-Grauer (Hybritech Corp., San Diego, Calif.), and mAb C219 (IgG$_{2a}$) from Centocor, Malvern, Pa.

All mAb samples were at least 95% pure according to SDS-PAGE. Concentrations of the mAb were determined by the quantitative mouse Ig radial immunodiffusion kit (ICN, Costa Mesa, Calif.). When necessary, mAb's were further concentrated and dialyzed against phosphate-buffered saline (PBS) or Dulbecco modified Eagle's medium (DMEM).

EXAMPLE 3

Derivation of the UIC2 Hybridoma

BALB/c mice were immunized with 1-2×10$^7$ of BALB/c 3T3-1000 cells from Example 1, injected s.c. and/or i.p. six times at two-week intervals. The final boosting was done with 2×10$^7$ cells i.p., and 5×10$^6$ cells i.v. Four days after the last administration of fibroblasts, the spleen from one animal was removed, and hybridomas with P3-X63-Ag8.653 human myeloma cells generated by art-recognized techniques. FITC-labeled goat anti-mouse polyvalent immunoglobulins (Sigma Chem. Co., St. Louis, Mo.) were used as a secondary antibody reagent at 1:100 dilution.

Tissue culture supernatant fluids from individual hybridomas were screened for mAb production by indirect immunofluorescence labeling of live BALB/c 3T3 and BALB/c 3T3-1000 cells attached to glass slides. Of 556 tested hybridomas, mAb produced by only two hybridomas reacted with BALB/c 3T3-1000 cells, and of these two only one hybridoma (termed UIC2) produced an antibody reactive with BALB/c 3T3-1000 cells, but not with control BALB/c 3T3 cells.

A stable hybridoma line secreting UIC2 mAb was established by three consecutive rounds of subcloning by endpoint dilution and screening of the supernatant fluids.

The UIC2 hybridoma was propagated as ascites in syngeneic BALB/c mice, and the immunoglobulin was purified from ascites fluid by Sepharose-Protein A (Bio-Rad, Richmond, Calif.) affinity chromatography. UIC2 mAb, tested by SDS-PAGE, was at least 95% pure IgG. The UIC2 hybridoma is on deposit in the American Type Culture Collection, Rockville, Md. (U.S.A.) (Accession No. HB11027, deposited with the American Type Culture Collection, 12301 Parklawn Drive, Rockville, Md. 20852 on Apr. 28, 1992) and will irrevocably and without restriction or condition be available to the public after this patent issues.

Application of Ouchterlony and immunoblotting tests using a standard set of anti-mouse Ig antibodies revealed that the UIC2 mAb belongs to the IgG$_{2a}$ subclass.

The ability of UIC2 mAb to induce complement-mediated cytotoxicity was tested by Low-Tox-M rabbit complement (Cedarlane Labs, Hornby, Ontario) on BALB/c, BALB/c 3T3-1000, CEM, CEM/VLB$_{100}$, K562 and K562/Inf cell lines.

EXAMPLE 4

Reactivity of UIC2 MAb with Human mdr1 Gene Product

Indirect Immunofluorescence Labeling.

UIC2 mAb was tested initially for reactivity with various Pgp-expressing cell lines by immunofluorescence staining. The cell lines tested and the results are shown in Table 1.

TABLE 1

| Cell Line | Description | UIC2 mAb reactivity |
|---|---|---|
| (i) Human, selected for MDR | | |
| KB-3-1 (parent) | Human epidermoid carcinoma | – |
| KB-8 | KB-3-1, colchicine-selected | +/– |
| KB-8-5 | KB-3-1, colchicine-selected | + |
| KB-8-5-11 | KB-3-1, colchicine-selected | ++ |
| KB-V1 | KB-3-1, vinblastine-selected | +++ |
| CEM (parent) | Human T-cell leukemia | – |
| CEM-VLB-100 | CEM, vinblastine-selected | ++ |
| (ii) Transfected with human mdr1 cDNA | | |
| K562 (recipient) | Human chronic myelogenous leukemia | – |
| K562/Inf | K562, infected with mdr1-expressing recombinant retrovirus | + |
| BALB/c 3T3 (recipient) | Mouse fibroblasts | – |
| BALB/c 3T3-1000 | Balb/c-3T3 transfected with human mdr1, vinblastine-selected | +++ |
| LR73 (recipient) | Chinese hamster ovary | – |
| LRMN1 | LR73, transfected with human mdr1 and neo genes, G418-selected | + |
| (iii) Green monkey kidney | | |
| CV1-COS | Green monkey kidney cells | + |
| (iv) Mouse, selected for MDR | | |
| J774.2 (parent) | Mouse macrophage cells | – |
| J7-V2-1 | J774.2, vinblastine-selected | – |
| J7-V3-1 | J774.2, vinblastine-selected | – |
| J7-C1-1000 | J774.2, colchicine-selected | – |

UIC2 mAb reacted with all tested human cell lines expressing the human mdr1 gene, including human or rodent cells transfected with human mdr1 cDNA and isolated with or without cytotoxic selection, as well as with CV1-COS green monkey cells known to express Pgp, but not with their drug-sensitive parents or any Pgp-negative cell line. The intensity of UIC2 mAb immunostaining correlated with the known levels of drug resistance in different cell lines. UIC2 mAb did not react with MDR derivatives of mouse J774.2 cells that express Pgp's encoded by each of the three mouse mdr genes, indicating that UIC2 mAb reactivity is primate-specific.

As noted above, K562/Inf cells were produced by retroviral transfer of the mdr1 gene and subcloning, without cytotoxic selection. Reactivity of UIC2 mAb with this cell line provides strong evidence that UIC2 mAb reacts with the mdr1 gene product, and not with some other cell marker produced by cytotoxic stress.

EXAMPLE 5

Isolation of Pgp by Immunoprecipitation

Transfected MDR cells ($5-10\times10^6$) were metabolically labeled with 50 µCi/ml of $^{35}$S-methionine (ICN) in methionine-free DMEM with 10% FCS, for 10-18 hours at 37° C. in 7% $CO_2$. After washing cells with PBS, they were incubated for 1 hour at room temperature with UIC2 mAb in 2.6 ml of PBS. The cells were then washed, and lysed (0.2% deoxycholic acid and 0.2 mM PMSF in PBS for 2-4 minutes). Lysates were clarified by centrifugation in a microfuge for 15 minutes at 4° C. The supernatant fluids were incubated with immobilized Protein A beads (Repligen, Cambridge, Mass.) for 1 hour at 4° C. with constant rotation. Protein A is a general adsorbent for IgG antibodies. After 5 washes of the sedimented beads with the lysing solution, beads were transferred to 40 µl of SDS-PAGE sample buffer, and the immunoprecipitated protein in SDS-PAGE was assayed for radioactivity and molecular weight by SDS-PAGE (7.5%).

These experiments showed that UIC2 mAb recognized a protein of 170-180 kDa expressed in MDR cells. This protein co-migrated on SDS-PAGE with one immunoprecipitated by Pgp-specific MRK-16 mAb under the same conditions, confirming that the antigen recognized by UIC2 mAb is human Pgp (FIG. 1).

Immunoprecipitation with UIC2 mAb was most successful when Pgp-containing plasma membranes were solubilized with deoxycholate; solubilization with the detergent CHAPS, which, although allowing efficient immunosedimentation of Pgp by MRK-16 mAb, effectively abolished the reactivity of Pgp with UIC2 mAb. This result suggests that UIC2 mAb and MRK-16 mAb recognize different epitopes on Pgp, with different sensitivity to detergents. UIC2 mAb, like MRK-16 mAb, did not react with denatured Pgp on Western blots under conditions in which Pgp was detectable by the C219 mAb which recognizes an intracellular, not-membrane-located epitope of this protein. N-octylglucoside (1%, Boehringer-Mannheim), although effective, was less so than deoxycholate for immunoprecipitation using UIC2 mAb.

The isolation procedure described above is flexible. For example, one can trypsinize Pgp-expressing target cells prior to solubilization, lyse them with detergent solution and then treat with the antibody and Protein-A beads. As noted above, protein A is a general adsorbent for IgG antibodies. Alternatively, it is possible to use Protein-A beads precoated with the antibody. Time and concentration parameters are also flexible. Any cell line, including those of animal or human origin, expressing human Pgp may be used as the target cell line.

EXAMPLE 6

Potentiation of Complement-Mediated Cytotoxicity by UIC2 Monoclonal Antibody

UIC2 mAb was tested for an ability to destroy multidrug-resistant BALB/c 3T3-1000 cells by an art-recognized complement-mediated cytotoxicity assay. In repeated experiments, from 70% to 80% of such cells were killed by UIC2 mAb.

EXAMPLE 7

Inhibition of Pgp-Mediated Efflux of Fluorescent Compounds by UIC2 mAb

The effect of mAb on the efflux of fluorescent compounds from MDR cells was studied by a flow cytometric assay.[15,44] In this assay, $10^6$ suspended cells were incubated with different mAb preparations at 20 µg/ml in 3-5 ml of serum-free medium for 30 minutes at 0° C., and then washed twice and loaded while cold with 0.5-1.0 µg/ml Rh123 for 10 minutes or with 5 µM doxorubicin for 1 hour. Rhodamine 123 (Rh123) is a mitochondrial fluorescent dye. MAb (20 µg/ml) was also added to dye-free medium during the efflux period at 37° C.; at this temperature, Pgp pumps Rh123 out of the cells. Dye retention after efflux was measured by fluorescence flow-cytometry.

Figure 2A:
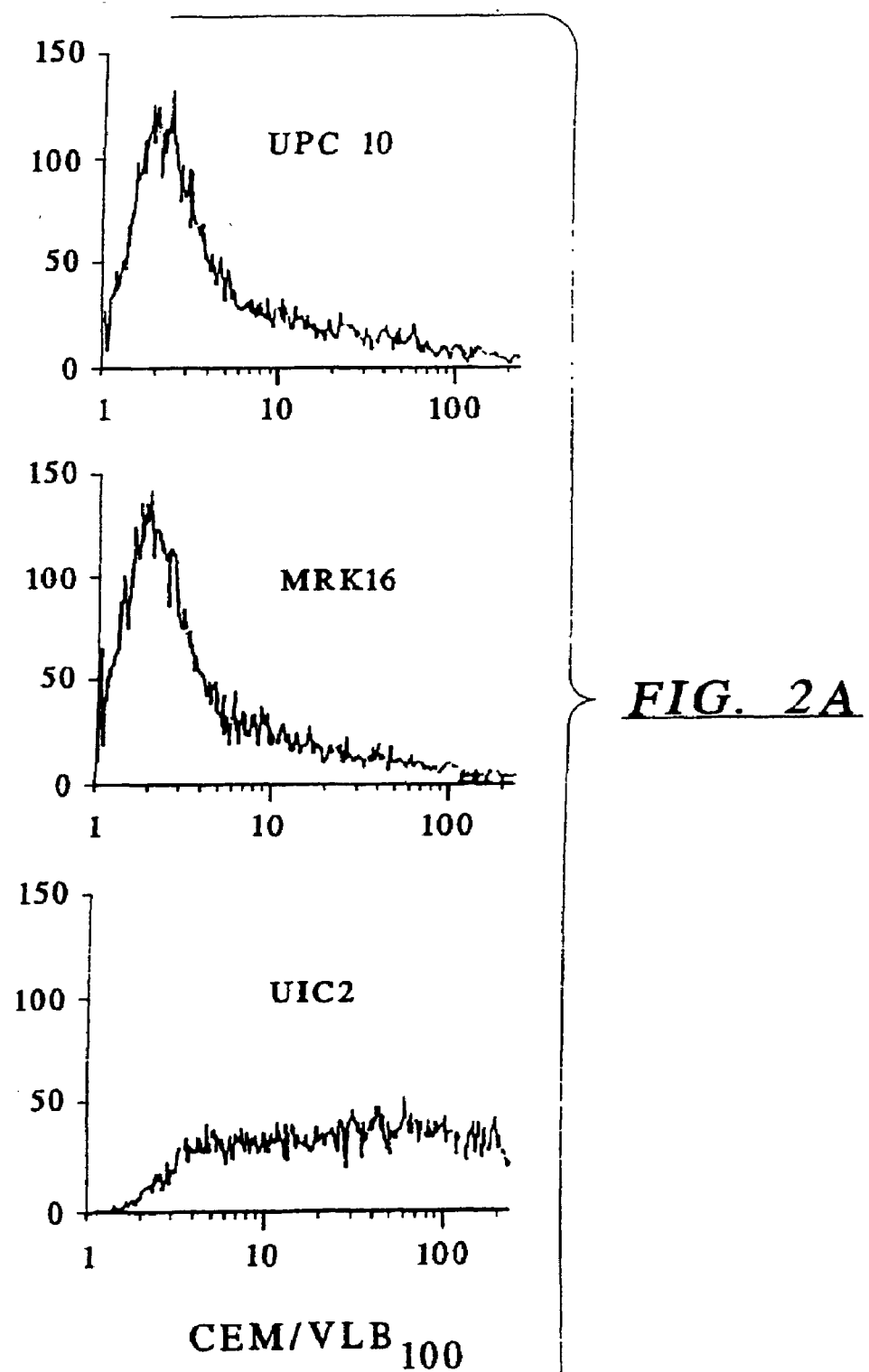
Figure 2B:
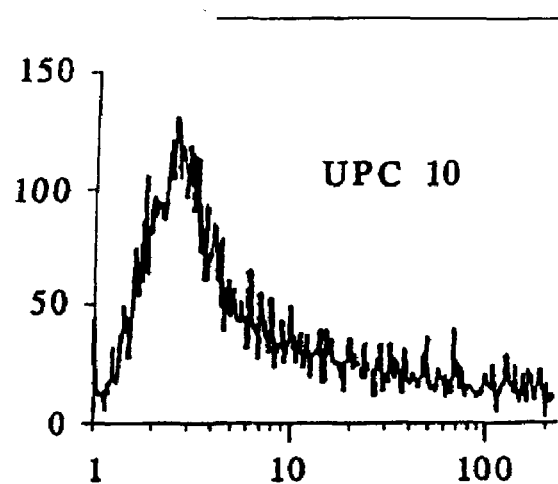
Figure 2B:
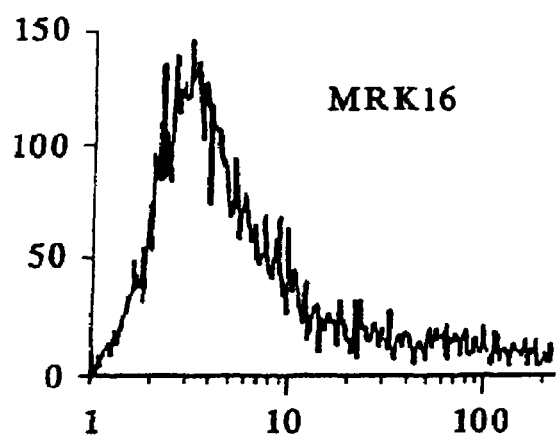
Figure 2B:
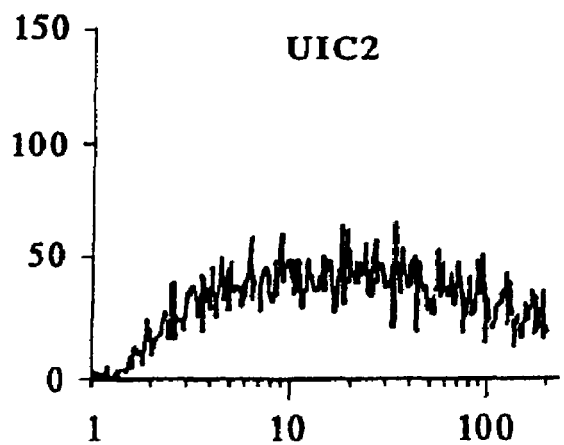

The effects of UIC2 mAb on the efflux of the Pgp-transported dye from MDR cells were determined. In the experiment of FIG. 2A, CEM/VLB$_{100}$ cells were loaded with 10 µg/ml Rh123 and incubated in dye-free media for 30 minutes at 37° C., in the presence of UIC2 mAb, MRK-16 mAb or UPC10 (control IgG$_{2a}$), and the cells analyzed by flow cytometry; cell fluorescence is plotted on a log scale. In the experiment of FIG. 2B, K562/Inf cells were loaded on ice with Rh123 at 1 µg/ml, and incubated as in 2A, except that the efflux time was 40 minutes. In the experiment of FIG. 2C, Rh123 efflux from K562/Inf cells was analyzed as in B (except that the efflux time was halved), in the presence of control IgG$_{2a}$ mAb (UPC10), UIC2 mab or UIC2 mAb pre-absorbed with anti-mouse IgG or anti-mouse IgM adsorbents.

In absorption experiments, UIC2 mAb at 20 µg/ml was incubated with 0.3 ml of agarose beads (Sigma) coupled covalently with affinity-purified goat anti-mouse IgG or anti-mouse IgM for 1 hour, and the absorbed material removed by centrifugation. UPC10 antibody (control IgG$_{2a}$) was used as the isotype control for UIC2 and MRK-16 mAb; purified whole mouse IgG was used as a control for HYB-241 and HYB-612 mAb.

UIC2 mAb did not alter the accumulation of a Pgp-transported dye Rh123 at 0° C. in MDR cells. However, at 20 µg/ml, this mAb significantly inhibited subsequent efflux of Rh123 at 37° C. from CEM/VLB$_{100}$ and K562/Inf cell lines, relative to controls treated with UPC10 IgG$_{2a}$ mAb (FIG. 2A, B). In sharp contrast, under the same conditions, MRK-16 mAb did not inhibit the efflux of Rh123 (FIG. 2A, B). Two other mAb preparations known to recognize cell surface human Pgp, namely, HYB-612 and HYB-241, also were without effect on Rh123 efflux, even though the intensity of immunofluorescent staining of all tested cell lines by UIC2, MRK-16, HYB-241 and HYB-612 antibodies was essentially the same. Concentrations of UIC2 mAb of 20 µg/ml were found to be saturating for all tested cell lines.

The inhibitory effect of UIC2 on Rh123 efflux from K562/Inf cells (FIG. 2C) and from CEM/VLB$_{100}$ cells was abolished after pre-absorption with anti-mouse IgG, but not with control anti-mouse IgM sorbent. This demonstrates that the material responsible for inhibition of Rh123 efflux was the antibody, and not non-IgG contaminants.

The same type of assay showed that UIC2 mAb decreased the efflux of a fluorescent anti-cancer drug, doxorubicin, from K562/Inf cells.

EXAMPLE 8

Reversal of Multidrug Resistance by UIC2 Monoclonal Antibody

All drugs were obtained from Sigma, except for G418 (Gibco) and taxol (gift of Dr. S. B. Horwitz). Colony formation and MTT assays for cell growth inhibition were carried out by art-recognized procedures. Effects of mAb on drug cytotoxicity were assayed by incubating cells growing in suspension or trypsinized monolayer cells with purified mab's, pre-dialyzed against DMEM, for 30 minutes at room temperature. Cells were plated in triplicate in 6-well tissue culture plates (Falcon Plastics, 200-250 cells/well for colony assays and 400-450 cells/well for MTT assays) in the presence of mAb. For MTT assays of K562/Inf cells, 96-well plates were used in quadruplicate. DMEM with 10% heat-inactivated FCS was used for all assays.

The effect of the UIC2 mAb on the resistance of two multidrug resistant cell lines to the anti-cancer drug vinblastine was tested in two different assay systems—cell growth and colony formation.

Figure 3A:
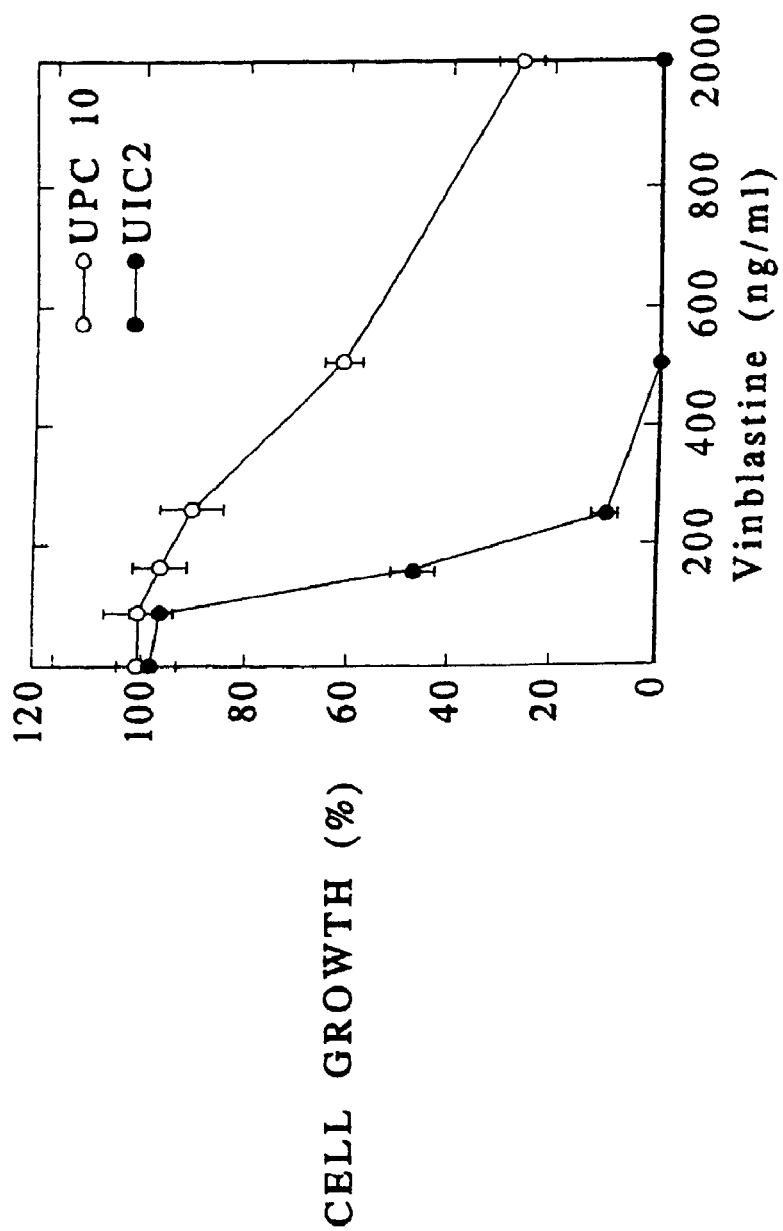
FIGS. 3A, 3B, 3C and 3D shows potentiation of vinblastine cytotoxicity by UIC2 mAb.

In the system described in FIG. 3A, inhibition of BALB/c 3T3-1000 fibroblast cell growth by different concentrations of vinblastine was tested in the presence of 20 µg/ml of UIC2 mab (•—•) or control IgG$_{2a}$ (UPC10) (o—o). All the values are expressed relative to UPC10 mab-treated BALB/c 3T3-1000 cells grown in the absence of the drug. All the assays were done in triplicate.

Figure 3B:
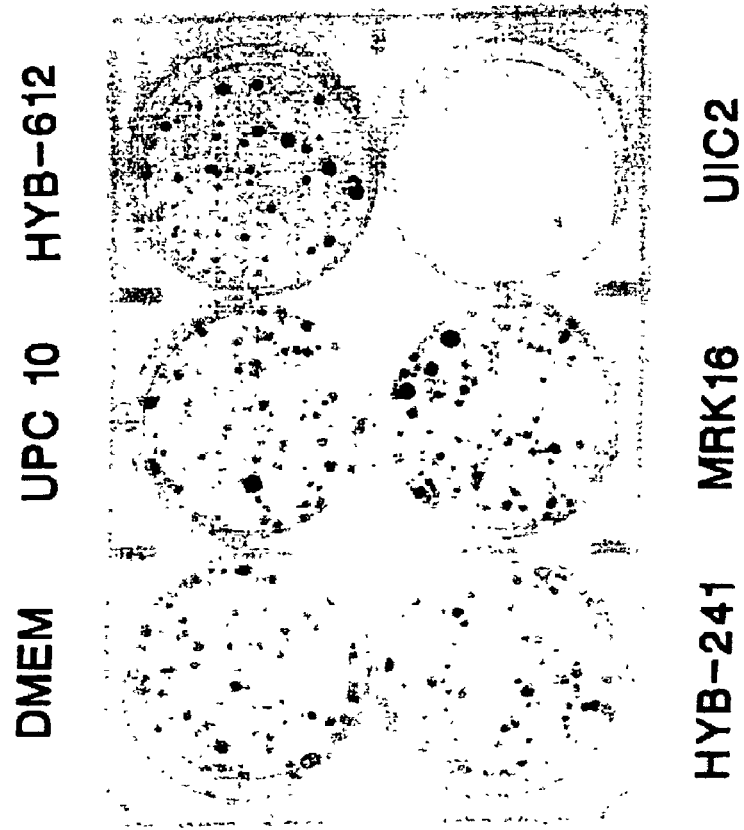

In the system described in FIG. 3B, we examined the effects of different mAb on colony formation by BALB/c 3T3-1000 fibroblasts in the presence of vinblastine. Cells (200 per well) were plated in 6-well Falcon dishes in the presence of 350 ng/ml of vinblastine (ID$_{90}$) and 20 µg/ml of the indicated mAb. Colonies were fixed with methanol or ethanol and stained with crystal violet on day 11, and scored for plating efficiency.

Figure 3C:
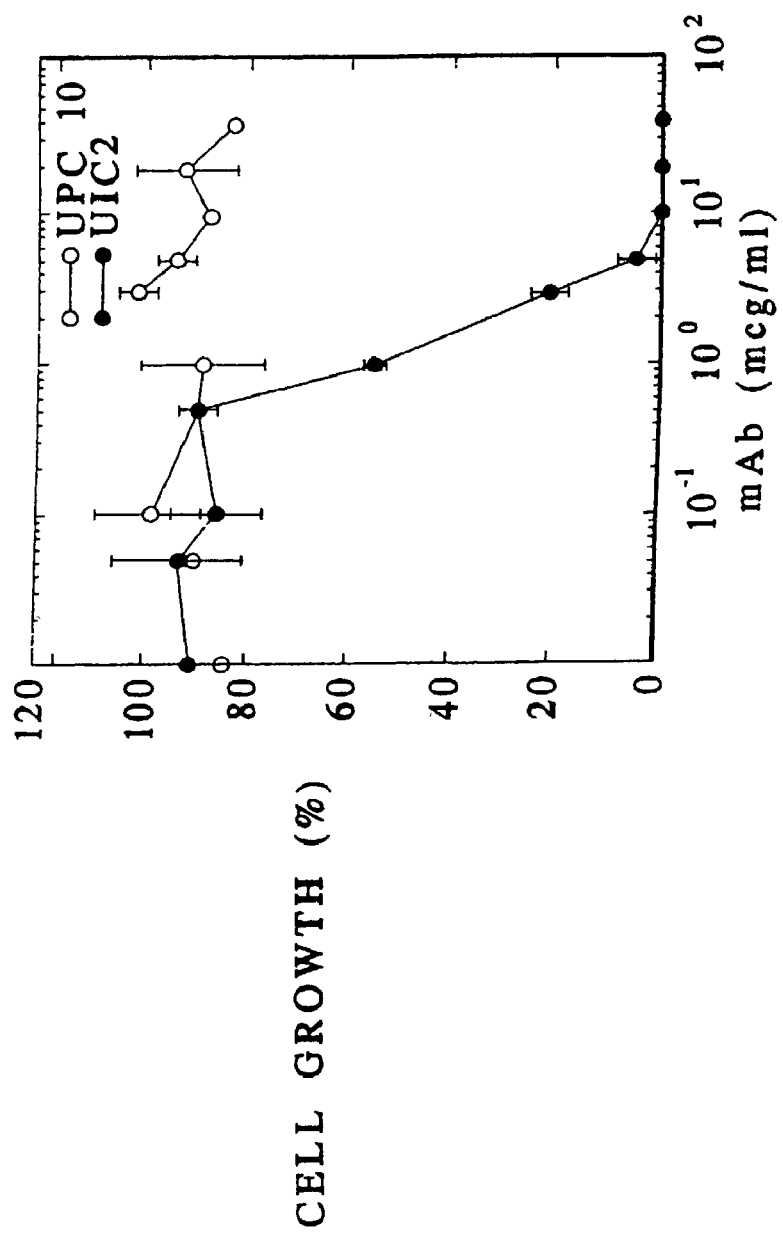

In the system described in FIG. 3C, we examined the effect of different concentrations of UIC2 mAb on BALB/c 3T3-1000 cell growth in the absence of vinblastine (o—o) or in the presence of 350 ng/ml of vinblastine (ID$_{90}$) (•—•). All of the values are expressed relative to control UPC10 IgG$_{2a}$-treated cells grown without vinblastine.

Figure 3D:
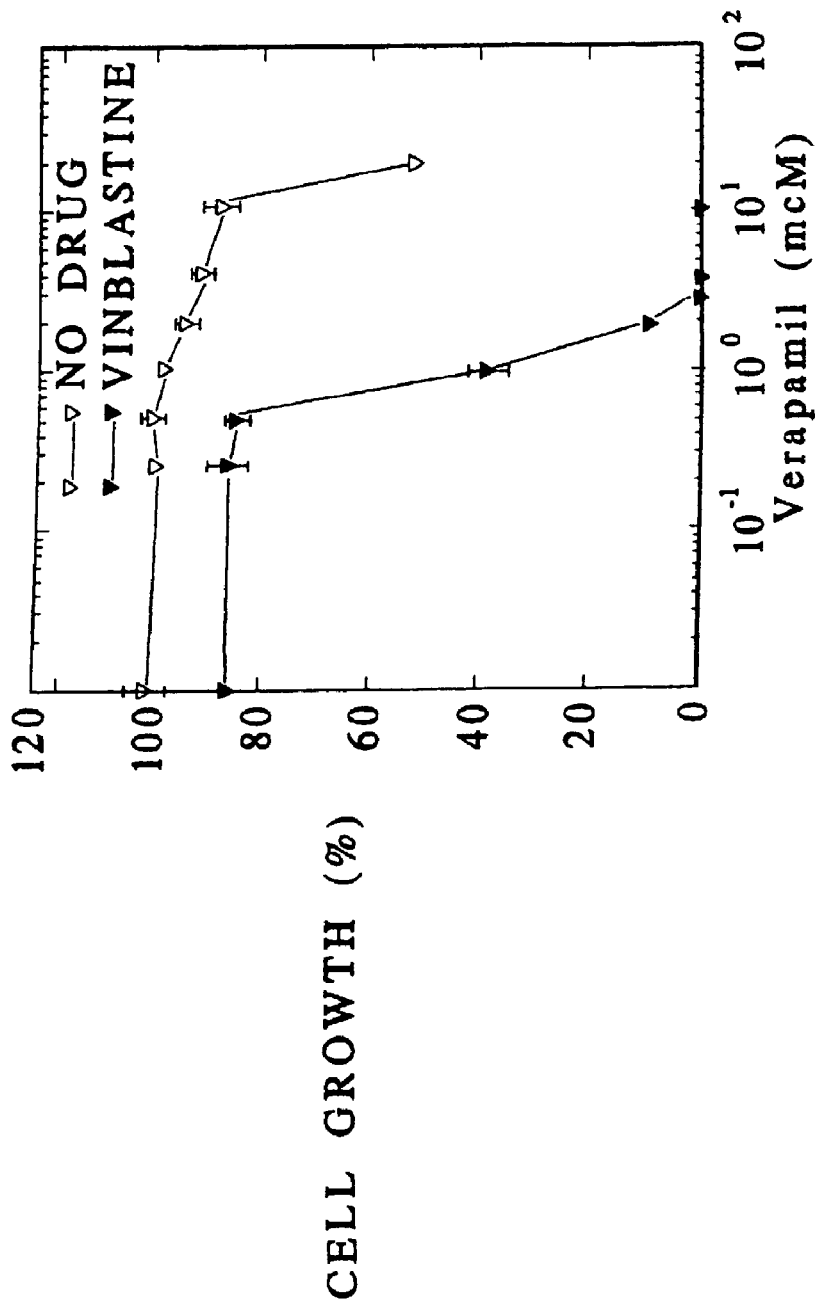

In the system described in FIG. 3D, we examined the effect of different concentrations of verapamil on the growth of BALB/c 3T3-1000 cells id the absence of vinblastine (o—o) or in the presence of 350 ng/ml of vinblastine (•—•).

Both UIC2 mAb and UPC10 IgG$_{2a}$ were desalted before use using ECONO-PAC® 10DG columns (Bio-Rad) equilibrated with serum-free DMEM medium, dialyzed against a large volume of medium or PBS, and filtered through Low Protein Binding 0.2 µm ACRODISC® filters (Gelman Sci. Co.).

In yet another test system, vinblastine resistance of K562/inf cells (made multidrug resistant as described in Example 1) growing in suspension culture was tested in a cell viability assay. Cells ($5 \times 10^3$ per well) were plated, in quadruplicate, in 96-well plastic plates (Falcon) in the presence of increasing concentrations of vinblastine plus 20 µg/ml of purified UIC2 mAb or control UPC10 IgG2a protein. After 6 days of incubation at 37° C. in 5% $CO_2$, cell viability was determined using the MTT assay.

As shown in FIG. 3A, the addition of UIC2 mAb strongly potentiated the inhibition of cell growth of BALB/c 3T3-1000 cells by vinblastine, decreasing the ID$_{50}$ value from 650 ng/ml to 150 ng/ml. In the absence of vinblastine, UIC2 mAb was without effect on cell growth.

The data of FIG. 3B illustrates that UIC2 mAb at 20 μg/ml completely inhibited colony formation by BALB/c 3T3-1000 cells in the presence of 350 ng/ml vinblastine (corresponding to the $ID_{90}$ for this cell line). In contrast, 3 other known anti-Pgp mAb's (MRK-16, HYB-241 and HYB-612) exerted no significant effect on cell growth or colony formation at the same concentration (FIG. 3C).

The potentiating effect of UIC2 mAb on the cytotoxicity of 350 ng/ml vinblastine in the 3T3-1000 cells became detectable at a mAb concentration as low as about 1 μg/ml, and UIC2 mAb completely suppressed all cell growth at 10 μg/ml (FIG. 3C). Verapamil, a well-characterized chemical inhibitor of Pgp, achieved the same potentiation of vinblastine toxicity only at concentrations as high as $3 \times 10^{-6}$ M (FIG. 3D).

UIC2 mAb also significantly decreased the level of drug resistance in all other tested cell lines, including K562/Inf, KB-GRC1 and KB-V1.

These findings indicate that UIC2 mAb, fragments, or recombinant derivatives containing the UIC2 $V_H$ and/or $V_L$ regions can be used to overcome multidrug resistance.

EXAMPLE 9

Pleiotropic Effect of UIC2 mAb on MDR

To determine if the potentiating effect of UIC2 mAb on cytotoxicity observed in Example 8 was limited to a specific subset of Pgp-transported drugs exemplified by vinblastine, we compared in this system nine drugs to which MDR cells are known to be resistant and which are known to have different mechanisms of cytotoxicity.

Figure 4:
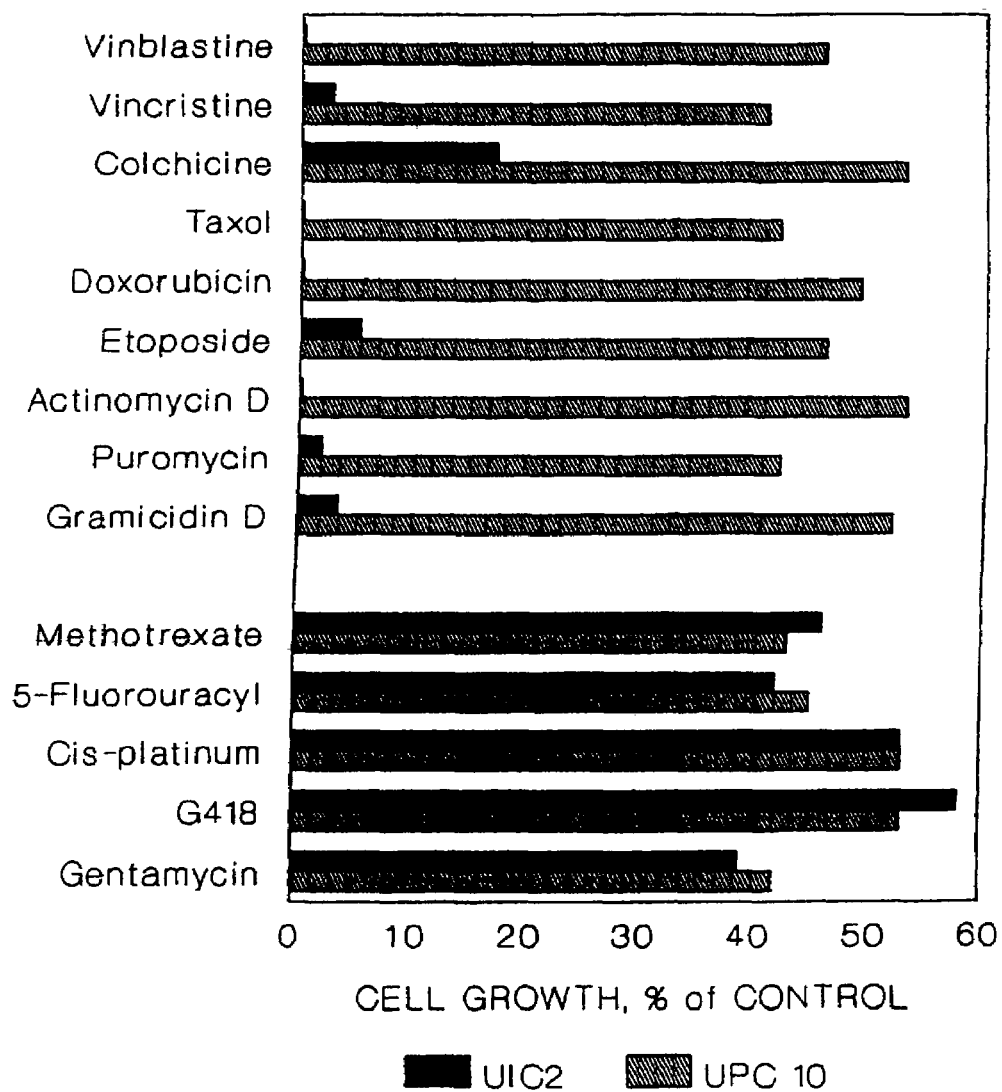
FIG. 4 shows potentiation of cytotoxic effects of different drugs by UIC2 mAb.

The bars in FIG. 4 represent the viability of BALB/c 3T3-1000 cells (as determined by the MTT assay) in the presence of 20 μg/ml of UIC2 mAb (solid bar) or UPC10 $IgG_{2a}$ control (hatched bar). The means of triplicate assays are shown; $SD_{mean}$ was <20% for each mean. Cell viability is expressed relative to that of control cells grown in the absence of drugs. Drug concentrations, corresponding to pre-determined $ID_{50}$ values were: vinblastine, 0.73 μM; vincristine, 3.2 μM; colchicine, 1 μM; taxol, 1.6 μM; doxorubicin, 0.4 μM; etoposide, 2.23 μM; actinomycin D, 0.06 μM; puromycin, 37.5 μM; gramicidin D, 4.1 μM; methotrexate, 0.04 μM; G418, 96 μM; gentamycin, 24 μM.

At the drug concentrations corresponding to $ID_{50}$ for BALB/c 3T3-1000 cells, 20 μg/ml UIC2 mAb greatly decreased cell growth in the presence of any one of the drugs to which MDR cells are known to be cross-resistant, including vinblastine, vincristine, colchicine, taxol, doxorubicin, etoposide, actinomycin D, puromycin and gramicidin D (FIG. 4). The inhibition of cell growth by UIC2 mAb relative to the UPC10 control ranged from 68% for colchicine to 100% for vinblastine, doxorubicin, actinomycin D and taxol. When a similar experiment was conducted at drug concentrations corresponding to the $ID_{20}$ values, UIC2 mAb inhibited cell growth by 97%-100% for all tested drugs (data not shown). UIC2 mAb had no effect on the cellular response to $ID_{50}$ doses of five cytotoxic drugs to which MDR cells are not cross-resistant, including methotrexate, 5-fluorouracil, cis-platinum, G418 and gentamycin (FIG. 4).

Thus, it can be concluded that the cytotoxicity-potentiating effect of UIC2 mAb is specific to Pgp substrates.

EXAMPLE 10

UIC2 mAb Epitope

It was demonstrated in Example 5 above that UIC2 mAb and MRK-16 mAb can be distinguished from each other by distinctions in the response of their respective epitope complexes to the same detergent.

It was demonstrated in Examples 7 and 8 above that UIC2 mAb efficiently inhibits the drug efflux function of Pgp, whereas other known monoclonal antibodies directed against extracellular epitopes on Pgp, such as MRK-16, HYB-241 and HYB-612, do not exhibit this property.

To further distinguish the epitopic region of UIC2 mAb from that of the other aforementioned monoclonal antibodies, Drs. A. Schinkel and P. Borst of the Netherlands Cancer Institute, Amsterdam, in collaboration with the inventors, compared reactivities of UIC2 mAb, MRK-16 mAb, HYB-241 mAb, and HYB-612 mAb with cell lines transfected by Drs. Schinkel and Borst with either normal mdr1 cDNA, mdr1 cDNA containing a deletion, or cDNA of the mdr2/mdr3 gene that is closely related to mdr1 cDNA but that does not confer drug resistance in cells.

Reactivity of the monoclonal antibodies with transfected cells was tested by our collaborators in a standard immuno-cytochemistry procedure. Adherent cells were removed from culture dishes by trypsinization, washed once in PBS, spotted on glass slides, then air-dried. For fixation of cells in formaldehyde, cells were rehydrated for 1 minute with PBS at room temperature (RT), and then fixed for 20 minutes in 10% formaldehyde in PBS (pH 7.2, 7° C.). Slides were rinsed in several changes of PBS at RT during 5-10 minutes, air-dried, and stored at −20° C. To stain fixed cells, the cells were rehydrated in PBS (RT, 10 minutes), incubated for 20 minutes at RT in PBS plus 1% (w/v) BSA plus normal goat serum (1:1000); after removing excess fluid by blotting, cell's were contacted with 8 μg/mL mAb in PBS (2 hours, RT). After 2 washes with PBS, cells were incubated for 30 minutes at RT with FITC-labeled goat-anti-mouse IgG (Tago, Burlingame, Calif.) diluted 1:50 in PBS/BSA, washed twice with PBS, and mounted in 80% (v/v) glycerine/20% (v/v) PBS, brought to pH 8.0 with TRIS base (glycerine is about 87% glycerol). The stained cells were then examined with a fluorescence microscope.

It was observed that UIC2 mAb reacted with cells that were transfected with full-length human mdr1 cDNA, but not with tMDR3.35 cells transfected with mdr2/mdr3 cDNA.[45] Further, UIC2 mAb did not react with transfectant cells that expressed a deleted form of human mdr1 cDNA. This deleted form encodes a Pgp with a deletion in the first extracellular loop of the following stretch of amino acids: IFANAGN-LEDLMSNITNRSD (Seq. ID No.: 1). In contrast, MRK-16 and HYB-241 mAbs reacted with such deletion transfectant.

The results indicate that the epitope recognized by UIC2 mAb is distinct from those recognized by previously known anti-Pgp monoclonal antibodies that do not possess the same biological functional activity and detergent reactivity of UIC2 mAb.

It is anticipated, therefore, that other monoclonal antibodies that recognize the UIC2 mAb epitope would also be able to inhibit the Pgp pump. Such monoclonal antibodies can readily be identified by their ability to react with cells transfected with full-length human mdr1 cDNA, coupled with a parallel inability to react with cells transfected with a mdr1 cDNA encoding Pgp containing a deletion within the above-shown stretch of amino acids.

Although the present invention has been described in terms of preferred embodiments, it is understood that variations and modifications will occur to those skilled in the art upon consideration of the present invention. Therefore, it is intended that all such equivalent variations and modifications should come within the scope of the invention as claimed.

REFERENCES

1. For general reviews, see Roninson, I. B., ed., *Molecular and Cellular Biology of Multidrug Resistance in Tumor Cells*, Plenum Press, N.Y., 1991; Gottesman, M. M., et al., in *Biochemical Bases for Multidrug Resistance in Cancer*, Academic Press, N.Y., 1991, Chapter 11.
2. Ford, J. M., et al., *Pharm. Rev.*, 42:155 (1990).
3. Akiyama, S.-i., et al., *Molec. Pharm.*, 33:144 (1988); Horio, M., et al., *PNAS(USA)*, 85:3580 (1988).
4. Cornwell, M. M. et al., *J. Biol. Chem.*, 261:7921 (1986); Tamai, I., *J. Biochem. Molec. Biol.*, 265:16509 (1990).
5. Ling, V., U.S. Pat. No. 4,837,306.
6. Hamada, H., et al., *PNAS(USA)*, 83:7785 (1986).
7. Pearson, J. W., et al., *J. Natl. Cancer Inst.*, 88:1386 (1991).
8. Tsuruo, T., et al., *Jpn. J. Cancer Res.*, 80:627 (1989).
9. Hamada, H., et al., *Cancer Res.*, 50:3167 (1990).
10. Meyers, M. B. et al., *Cancer Res.*, 49:3209 (1987); O'Brien, J. P. et al., *Proc. Amer. Assoc. Cancer Res.*, 30:Abs 2114 (1989).
11. Cinciarelli, C., et al., *Int. J. Cancer*, 47:533 (1991).
12. Roninson, I. B., et al., U.S. patent application Ser. No. 622,836, effective filing date Mar. 28, 1986.
13. Choi, K., et al., *Cell*, 53:519 (1988).
14. Kearney, J. F., et al., *J. Immunol.*, 123:1548 (1979).
15. Chaudhary, P. M., et al., *Cell*, 66:85 (1991).
16. Pawels, R., *J. Virol. Meth.*, 20:309 (1988).
17. Bruggeman, M., et al., *J. Exp. Med.*, 166:1351 (1987).
18. Nilsson, B. O., et al., *Immunol. Today*, 11:10 (1990).
19. Barrebaeck, C. A. K., et al., *Adv. Drug Devel. Rev.*, 2:143 (1988); Pollock, B., et al., *Lab. Meth. Immunol.*, 1:51 (1990); Vaux, D., et al., *Technique (Phila.)* 2:72 (1990); and, Gathura, J. K., et al., *J. Immunol. Meth.*, 137:95 (1991).
20. Winter, G., et al., *Nature*, 349:293 (1991).
21. Oriandi, R., et al., *PNAS (USA)*, 86:3833 (1989).
22. Sambrook, et al., eds., *Molec. Cloning: A Laboratory Manual*, Cold Spring Harbor Laboratory, Cold Spring Harbor, N.Y., 1989.
23. Reichmann, L., et al., *Nature*, 332:323 (1988).
24. Jones, P. T., et al., *Nature*, 321:522 (1986).
25. Vorhoeyen, M., et al., *Science*, 239:1534 (1988).
26. Queen, C., et al., *PNAS (USA)*, 86:10029 (1989).
27. Harlow, E., et al., eds., *Antibodies: A Laboratory Manual*, Cold Spring Harbor Laboratory, Cold Spring Harbor, N.Y., 1988.
28. Chiang, Y. L., et al., *Biotechniques*, 7:360 (1989).
29. Glockshuber, R., et al., *Biochem.*, 29:1362 (1990).
30. Bird, R. E., et al., *Science*, 242:423 (1988); Ladner, R. C., et al., U.S. Pat. No. 4,946,778, Aug. 7, 1990; Huston, J. S., et al., *PNAS(USA)*, 85:5879 (1988).
31. Foon, K. A., *Cancer Res.*, 49:1621 (1989).
32. McCafferty, J., et al., *Nature*, 348:552 (1990).
33. Charbit, A., et al., *Gene*, 70:181 (1988).
34. Nolan, O., et al., *Biochim. Biophys. Acta*, 1040:1 (1990); Sonasivilai, S., et al., *Clin. Exp. Immunol.*, 79:315 (1990).
35. Barrebaeck, C. A. K., *Immunol. Today*, 9:355 (1988); Barrebaeck, C. A. K., *J. Immunol. Meth.*, 123:157 (1989).
36. Kohler, H., et al., *Meth. Enzymol.*, 178:3 (1989).
37. Bhattacharya-Chattayee, et al., *J. Immunol. Meth.*, 141: 1398 (1988).
38. Georges, E., et al., Abstract, Posner Session A, *Amer. Assoc. Cancer Res.*, Mar. 11, 1991.
39. Young, R. A., et al., *PNAS (USA)*, 82:2583 (1985).
40. Hoeffler, H., et al., *Histochem. J.*, 18:597 (1986).
41. Gennaro, A. R., ed., *Remington's Pharmaceutical Sciences*, 18th ed., Mack Publishing Co., Easton, Pa., 1990.
42. Choi, K., et al., *PNAS(USA)*, 88:7386 (1991).
43. Hsu, S. I. et al., *J. Biochem. Molec. Biol.*, 264:12053 (1989).
44. Neyfakh, A. A., *Exp. Cell Res.*, 174:168 (1988).
45. Schinkel, A. H., et al., *Cancer Res.*, 51:2628 (1991).

---

---

We claim:

1. An isolated peptide that is an immunospecific epitope of an antibody produced by a hybridoma cell identified as UIC2 hybridoma (ATCC Accession No. HB11027), wherein the peptide consists of the amino acid sequence identified by SEQ ID NO: 1.

* * * * *

UNITED STATES PATENT AND TRADEMARK OFFICE
CERTIFICATE OF CORRECTION

PATENT NO. : 7,598,340 B2  
APPLICATION NO. : 10/292541  
DATED : October 6, 2009  
INVENTOR(S) : Metchetner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 711 days.

Signed and Sealed this

Twenty-eighth Day of September, 2010

David J. Kappos  
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: PRT
<213> ORGANISM: Homo sapiens

<400> SEQUENCE: 1

Ile Phe Ala Asn Ala Gly Asn Leu Glu Asp Leu Met Ser Asn Ile Thr
            5                   10                  15

Asn Arg Ser Asp
        20
```